(12) United States Patent
Belanger et al.

(10) Patent No.: US 11,298,138 B2
(45) Date of Patent: Apr. 12, 2022

(54) HEMOSTATIC DEVICE

(71) Applicant: TCI MS LTD, Providenciales (TC)

(72) Inventors: Guy Belanger, St-Bruno (CA);
Normand Mercier, Sant-Damien de Buckland (CA)

(73) Assignee: TCI MS LTD, Providenciales (TC)

( * ) Notice: Subject to any disclaimer, the term of this patent is extended or adjusted under 35 U.S.C. 154(b) by 146 days.

(21) Appl. No.: 16/653,100

(22) Filed: Oct. 15, 2019

(65) Prior Publication Data

US 2020/0038039 A1 Feb. 6, 2020

Related U.S. Application Data

(63) Continuation-in-part of application No. 16/270,867, filed on Feb. 8, 2019, now abandoned.

(30) Foreign Application Priority Data

Feb. 8, 2018 (CA) .............................. CA 2994315

(51) Int. Cl.
*A61B 17/132* (2006.01)
*A61B 17/00* (2006.01)
*A61B 17/12* (2006.01)

(52) U.S. Cl.
CPC ...... *A61B 17/1325* (2013.01); *A61B 17/0057* (2013.01); *A61B 2017/00654* (2013.01); *A61B 2017/12004* (2013.01)

(58) Field of Classification Search
CPC .............. A61B 17/132; A61B 17/1322; A61B 17/1325; A61B 17/1327
See application file for complete search history.

(56) References Cited

U.S. PATENT DOCUMENTS

| 5,728,120 A * | 3/1998 | Shani ................. A61B 17/1325 606/120 |
|---|---|---|
| 8,353,927 B2 | 1/2013 | Lampropoulos et al. |
| 9,107,671 B2 | 8/2015 | Guillot |
| 2005/0125025 A1* | 6/2005 | Rioux ................. A61B 17/0057 606/201 |
| 2009/0281565 A1* | 11/2009 | McNeese ............ A61B 17/1327 606/201 |
| 2010/0280541 A1* | 11/2010 | Lampropoulos ..... A61B 17/132 606/203 |
| 2011/0196417 A1 | 8/2011 | Clark |

(Continued)

FOREIGN PATENT DOCUMENTS

| GB | 8900 | 6/1916 |
|---|---|---|
| WO | 2003099350 | 12/2003 |

*Primary Examiner* — Shaun L David (57) ABSTRACT

An hemostatic device, the hemostatic device comprising: a bracelet configurable between an open configuration and a closed configuration, wherein, in the closed configuration, the bracelet forms a loop and in the open configuration, the bracelet is linear; a compression element mounted to the bracelet and defining a compression surface for compressing against a patient, the compression element being movable relative thereto the bracelet so that a distance between the bracelet and the compression surface is varied when the bracelet and compression element are moved relative to each other, the compression element including a lock for selectively locking the compression element and bracelet relative to each other.

15 Claims, 9 Drawing Sheets

(56) References Cited

U.S. PATENT DOCUMENTS

| | | | |
|---|---|---|---|
| 2011/0202089 A1* | 8/2011 | Sun .................... | A61B 17/1325 |
| | | | 606/201 |
| 2011/0295310 A1* | 12/2011 | Bao .................... | A61B 17/1325 |
| | | | 606/203 |
| 2012/0191127 A1* | 7/2012 | Guillot ............... | A61B 17/1327 |
| | | | 606/203 |
| 2014/0031861 A1* | 1/2014 | Teeslink ............. | A61B 17/1325 |
| | | | 606/213 |

* cited by examiner

HEMOSTATIC DEVICE

FIELD OF THE INVENTION

The present invention relates to the general field of medical devices and is particularly concerned with an hemostatic device for hemostatically sealing percutaneous vascular punctures.

BACKGROUND

There exists a plurality of medical and/or surgical procedures that are carried out intravascularly or intralumenally. For example, in the treatment of vascular diseases, such as atherosclerosis, percutaneous angioplasty and stenting are now widely accepted procedures.

Such procedures usually involve the percutaneous puncture and insertion of various surgical instruments in the puncture. When the procedure is completed, all the surgical instruments are removed, leaving a puncture site in the vessel wall. Such procedures hence unavoidably present the problem of stopping the bleeding at the percutaneous puncture site after the procedure has been completed and after the instruments and any introducer sheaths used therewith have been removed. To that effect, pressure is applied at the puncture site. This pressure must be applied until natural body repair mechanisms block blood flow. For example, this pressure must be applied for one hour or more.

Many devices have been conceived to apply this pressure using a compression pad. Such devices may include adjustable pads mounted to a bracelet. Once the bracelet is secured to the patient, the adjustable pads can be adjusted to achieve a desired pressure on the vessel. Since application of a suitable pressure is an important factor in prompt and safe hemostasis, accidental movements of the pads relative to the bracelet, which would affect the pressure selected by the surgeon or nurse who applied the bracelet, are highly undesirable.

Accordingly, there exists a need for an improved hemostatic device for hemostatically sealing percutaneous vascular punctures. It is a general objective of the present invention to provide such an improved hemostatic device.

SUMMARY OF THE INVENTION

In a broad aspect, the invention provides an hemostatic device, the hemostatic device comprising: a bracelet configurable between an open configuration and a closed configuration, wherein, in the closed configuration, the bracelet forms a loop and in the open configuration, the bracelet is linear; a compression element mounted to the bracelet and defining a compression surface for compressing against a patient, the compression element being movable relative thereto the bracelet so that a distance between the bracelet and the compression surface is varied when the bracelet and compression element are moved relative to each other, the compression element including a lock for selectively locking the compression element and bracelet relative to each other.

In another broad aspect, the invention provides a hemostatic device, the hemostatic device comprising: a bracelet for enclosing a limb of a patient; a compression element mounted to the bracelet and defining a compression surface for compressing against the patient, the compression element being movable relative thereto the bracelet so that a distance between the base and the compression surface is varied when the bracelet and compression element are moved relative to each other; and an actuator for selectively moving the compression element relative to the bracelet between a retracted position and an extended position, wherein the compression surface is closer to the bracelet in the retracted position than in the extended position; and a lock for selectively locking the compression element and bracelet relative to each other so as to prevent movements between the retracted and extended positions.

There may also be provided a hemostatic device wherein the lock is operative for selectively locking the compression element and bracelet relative to each other at discrete positions between the extended and retracted positions.

There may also be provided a hemostatic device wherein the compression element is a radial artery compression element configured and sized for compressing a radial artery, the actuator being a radial artery actuator, the hemostatic device further comprising an ulnar artery compression element configured and sized for compressing an ulnar artery and an ulnar artery actuator for selectively moving the compression element relative to the bracelet.

There may also be provided a hemostatic device wherein the bracelet includes a base defining a pair of threaded actuator mounting apertures extending therethrough and the radial and ulnar artery compression elements each including a respective compression pad, the radial and ulnar actuators each including a respective threaded stem threadedly engaging a respective one of the actuator mounting aperture and also engaging a respective one of the compression pads so that rotating the threaded stems relative to the base changes a distance between the compression pads and the base.

There may also be provided a hemostatic device wherein the radial and ulnar artery compression elements are mounted to the base so as to be circumferentially spaced apart from each other when the bracelet is in a closed configuration, facing radially inwardly, towards a centre of a loop formed by the bracelet.

There may also be provided a hemostatic device wherein the bracelet includes a base defining substantially opposed base first and second ends, the compression element further including a compression pad defining the compression surface, the actuator engaging the base and the compression pad so that the actuator is usable to vary a distance between the compression pad and the base.

There may also be provided a hemostatic device wherein the base defines an actuator mounting aperture extending therethrough, the actuator mounting aperture being threaded, the actuator including a threaded stem threadedly engaging the actuator mounting aperture and also engaging the compression pad so that rotating the threaded stem relative to the base changes a distance between the compression pad and the base.

There may also be provided a hemostatic device wherein the threaded stem is substantially perpendicular to a circumferential direction extending between the base first and second ends.

There may also be provided a hemostatic device wherein the threaded stem is operatively coupled to the compression pad so as to be rotatable relative thereto and axially fixed relative thereto so that the compression pad is movable axially relative to the base as the threaded stem is rotated in the actuator mounting aperture while maintaining a fixed orientation relative to the base.

There may also be provided a hemostatic device wherein the base further defines a pair of pad mounting aperture extending therethrough each extending parallel to the stem mounting aperture; and the compression pad further includes a pair of pad stems extending opposed to the compression surface, each pad stems being substantially snugly received in one of the pad mounting apertures so as to be longitudinally movable therealong.

There may also be provided a hemostatic device wherein the compression pad defines a generally cylindrical recess and an opening leading into the recess, the opening being smaller in diameter than a remainder of the recess, the threaded stem being terminated by a head engaging the recess and maintained therein, the head being rotatable relative to the recess so that the threaded stem may be rotated relative to the base while maintaining fixed a relative orientation between the base and the compression pad.

There may also be provided a hemostatic device wherein the threaded stem is provided with a wing opposed to the head compression surface.

There may also be provided a hemostatic device wherein the lock includes a pin mounted to the actuator so as to be movable relative to the threaded stem, the base defining lock apertures formed in the base facing the pin, the lock apertures being provided in one of a generally circular shaped configuration and a generally arc segment shaped configuration centred on the actuator mounting aperture, the lock apertures being configured and sized to receive the pin so that with the pin received in one of the lock apertures, rotation of the threaded stem relative to the base is prevented, and with the pin withdrawn from the lock apertures, the threaded stem is rotatable relative to the base.

There may also be provided a hemostatic device wherein indicia are provided adjacent each lock aperture to identify each lock aperture, each indicia being indicative of a relative distance between the base and the compression pad.

There may also be provided a hemostatic device wherein the pin is movable relative to actuator substantially parallel to the threaded stem between a lowered position, wherein the pin is engaged in one of the lock apertures, and a raised position, wherein the pin is spaced apart from the base.

The hemostatic device as defined in claim 15, wherein the pin is mounted in a pair of spaced apart pin collars formed in the actuator, the pin including a pin stem inserted in the pin collars and terminated by pin head, a pin protrusion extending laterally from the pin stem, the pin head and pin protrusion limiting movements of the pin stem in the pin collars between the raised and lowered positions.

There may also be provided a hemostatic device wherein the bracelet further includes a flexible strap extending from the base first end and a closure provided as the base second end, the closure and strap being configured and sized so that the strap is engageable in the closure to close the bracelet to form a loop.

There may also be provided a hemostatic device wherein the strap is provided with a deformable portion compressible to provide a cushion when tightened around a wrist of a patient.

Advantageously, the proposed bracelet allows adjustment of the compression pressure on the patient without tightening or loosening the bracelet. Instead, the compression pressure is adjusted by moving the compression element relative to the bracelet, while ensuring though the lock that accidental reductions in compression pressure are not possible, or at least very rare. Also, in some embodiments, the proposed device had a lock that is relatively difficult to operate using only one hand, which makes it difficult for a patient wearing the bracelet around a wrist to release voluntarily the pressure exerted by the bracelet without the assistance of medical personnel. This is useful as a lengthy compression at the puncture site may be uncomfortable, and a patient may wish to reduce the compression pressure before blood flow through the puncture has been stopped.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the drawings:

FIG. 5, in a perspective cross-sectional partial view, illustrates the hemostatic device of FIGS. 1 to 4;

FIG. 6, in an alternative perspective cross-sectional partial view, illustrates the hemostatic device of FIGS. 1 to 5;

FIG. 8, in an alternative perspective cross-sectional partial view, illustrates the hemostatic device of FIGS. 1 to 7;

DETAILED DESCRIPTION

Terms such as "substantially", "about" and "essentially" are used throughout this document to indicate variations in the thus qualified terms. These variations are variations that do not materially affect the manner in which the invention works and can be due, for example, to uncertainty in manufacturing processes or to small deviations from a nominal value or ideal shape that do not cause significant changes to the invention. These variations are to be interpreted from the point of view of the person skilled in the art.

Figure 1:
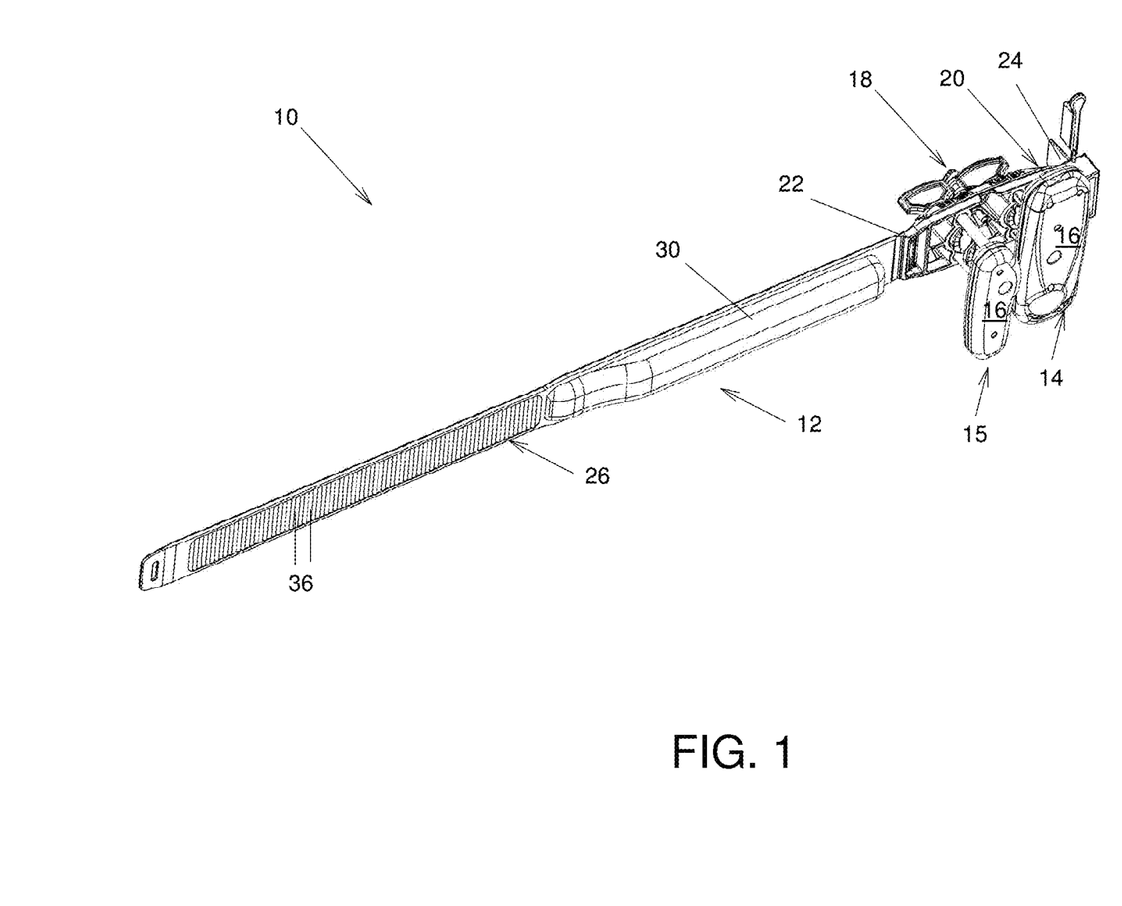
FIG. 1, in a perspective view, illustrates an hemostatic device in accordance with an embodiment of the present invention.

Referring to FIG. 1, there is shown a hemostatic device 10 in accordance with an embodiment of the present invention. The hemostatic device 10 is usable for substantially hemostatically sealing a percutaneous puncture in a blood vessel of a patient and is usable to encircle a limb of a patient.

Figure 9:
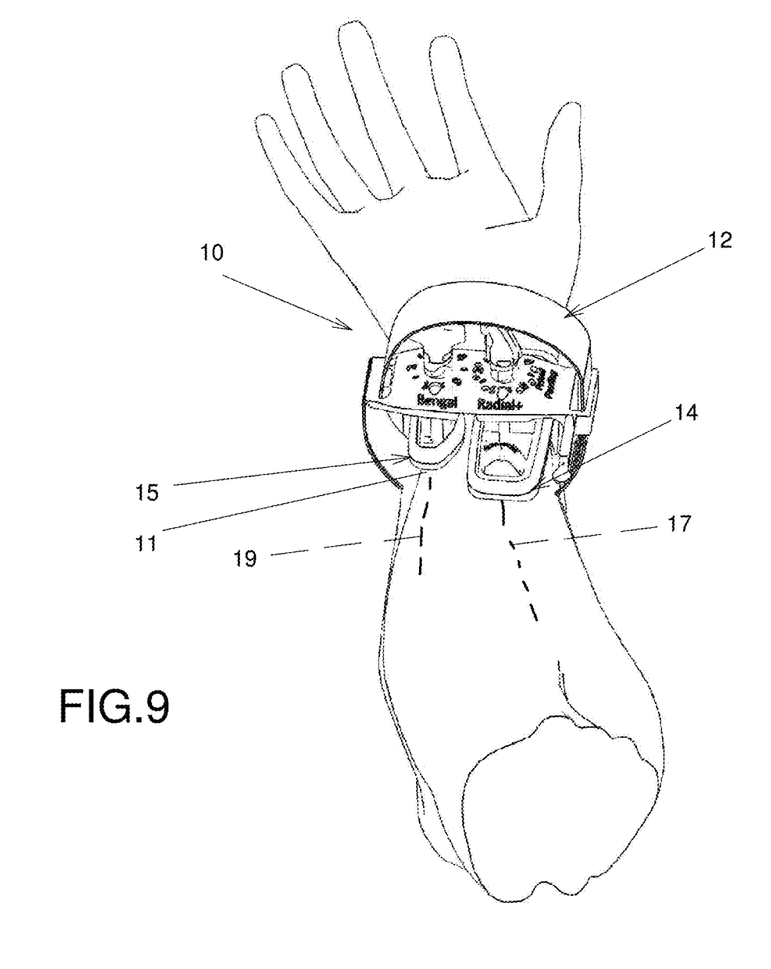
FIG. 9, in a perspective view, illustrates the hemostatic device of FIGS. 1 to 8 secured to a wrist of a patient.

The hemostatic device 10 includes a bracelet 12 configurable between an open configuration (seen in FIGS. 1 to 8) and a closed configuration (seen in FIG. 9). In the closed configuration, the bracelet 12 forms a loop and in the open configuration, the bracelet 12 is linear. A compression element 14 is mounted to the bracelet 12 and define a compression surface 16 for compressing against the patient. The compression element 14 is movable relative to the bracelet 12 so that a distance between the bracelet 12 and the compression surface 16 is varied when the bracelet 12 and the compression element 14 are moved relative to each other. The compression element 14 including a lock 18 for selectively locking the compression element 14 and bracelet 12 relative to each other.

In some embodiments, as shown in FIG. 9 for example, the hemostatic device 10 includes two compression elements 14 and 15. These embodiments are usable for example around the wrists 11 of patients to exert pressure on both the radial and ulnar arteries 17 and 19. However, any suitable number of compression elements 14 and 15 is usable in the present invention, for example only one compression element or more than two compression elements. Also, similar devices usable at other locations on a patient are also within the scope of the invention. Furthermore, only some or all of the compression elements 14 and 15 may be provided with the lock 18. In the embodiment shown in the drawings, only the compression element 14 is provided with the lock 18 as compression of the ulnar artery 19, which is typically not punctured but compressed only to assist in hemostatis of the punctured radial artery, is not as critical as compression of the radial artery.

Referring to FIG. 1 for example, the bracelet 12 includes a substantially rigid base 20 defining substantially opposed base first and second ends 22 and 24. A flexible strap 26 extends from the base first end 22 and a closure 28 is provided as the base second end 24. The compression elements 14 and 15 are mounted to the base 20 as further described hereinbelow. The closure 28 and strap 26 are configured and sized so that when the bracelet 12 is in the closed configuration, the strap 26 engages the closure 28 to maintain the closed configuration.

The strap 26 may be provided with a deformable portion 30 that is compressible to provide a cushion when tightened around the wrist of a patient. However, in other embodiments, the deformable portion 30 is omitted and either replaced by a gel, foam or other deformable material secured to the strap 26, or completely omitted without any replacement structure.

A specific example of the closure 28 and the corresponding structures on the strap 26 are now described briefly. These structures are described in greater detail in PCT application PCT/CA2011/000903 filed on Aug. 9, 2011, the contents of which is hereby incorporated by reference in its entirety. It should be noted that other bracelet that allow enclosing safely a limb of a patient are also usable in alternative embodiments of the invention.

Figure 5:
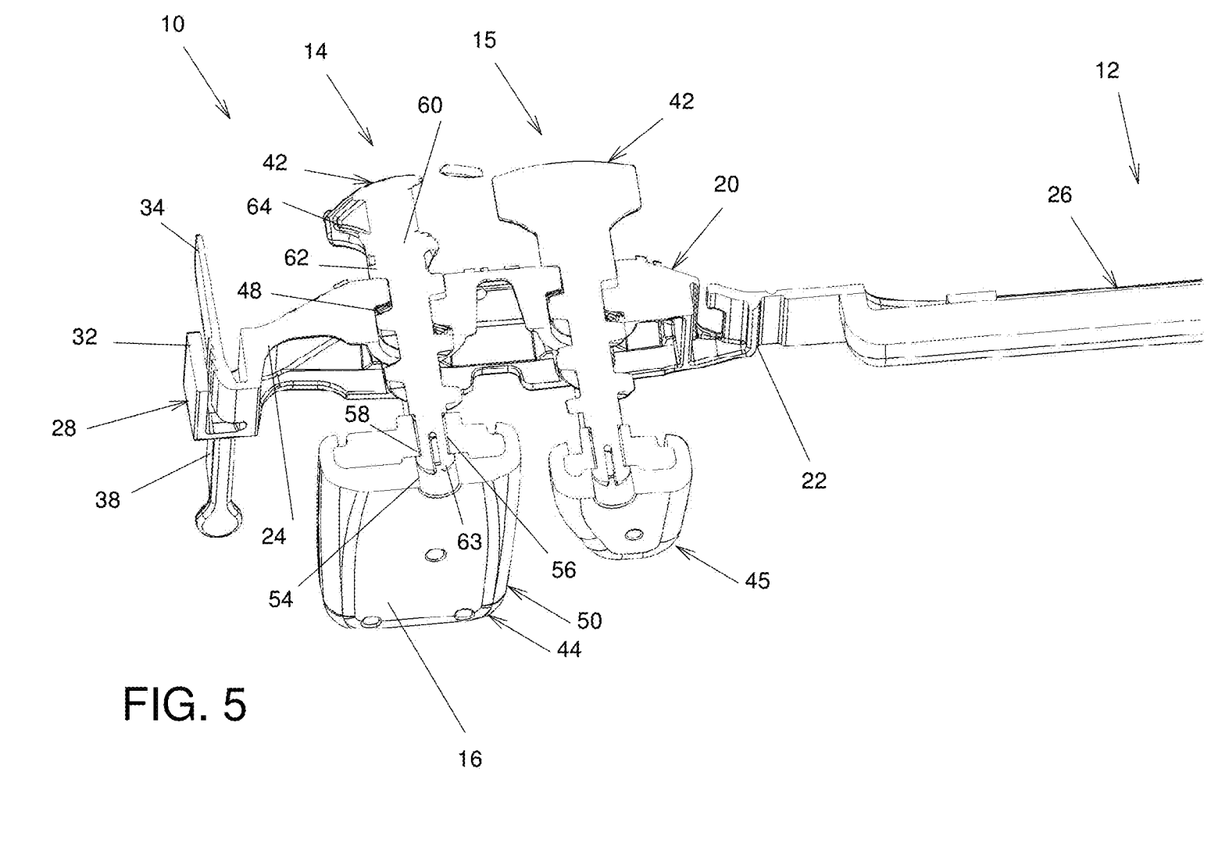
Figure 6:
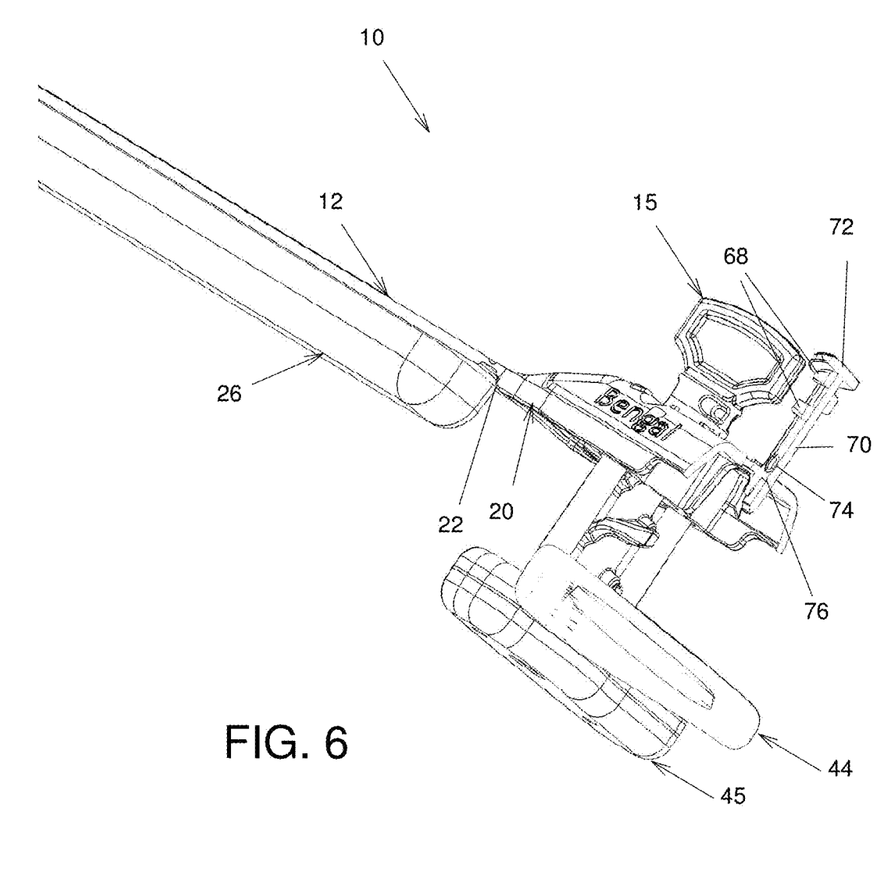

Referring for example to FIG. 5, the closure 28 defines a collar 32 through which the strap 26 is insertable. The closure 28 also includes a flexible tongue 34. The strap 26 is provided with ribs 36 (seen in FIG. 1) opposed to the base 20. The ribs 36 face the tongue 34 when the bracelet 12 is in the closed configuration are configured to engage the tongue 34 so that tightening of the strap 26 is easily achieved while loosening of the strap 26 requires manual deflection of the tongue 34 to disengage the strap 26, and more specifically the ribs 36. To that effect, the tongue 34 is also ribbed and the ribs of the tongue 34 and strap 26 are configured to easily slide over each other through slanted surfaces when the bracelet 12 is tightened, while interfering with each other, for example with surfaces that are perpendicular to each other, when an attempt to loosen the bracelet 12 is made. This type of mechanism is similar to the well known zip ties and similar devices. In some embodiments, the closure 28 is provided with a block 38 insertable in the collar 32 to prevent movements of the tongue 34, so that accidental loosening of the strap 26 is unlikely. More details regarding the closure 28 and the corresponding structures on the strap 26 are provided in the above-referenced PCT patent application.

The compression elements 14 and 15 are mounted to the base 20 so as to be circumferentially spaced apart from each other when the bracelet 12 in the closed configuration, with their compression surfaces 16 facing radially inwardly, towards the centre of the loop formed by the bracelet 12. The compression elements 14 and 15 are substantially similar, except for the omission of the lock 18 in the compression element 15. Only the compression element 14 and the corresponding structures on the base 20 are therefore described in details herein, with the assumption that similar structures and provided for the compression element 15.

Referring to FIGS. 2 to 5, the compression element 14 includes an actuator 42 and a compression pad 44, the latter defining the compression surface 16. The compression element 15 may includes a compression pad 45 that is similar in shape to the compression pad 44, or may include a compression pad 45 that differs in shape from the compression pad 44 to accommodate the functionality of the compression pad 45. The compression pad 44 is mounted to the base 20 so as to be movable relative thereto in a direction generally radial when referring to the closed shape of the bracelet 12. This direction is typically perpendicular to a line joining the base first and second ends 22 and 24. The actuator 42 is operatively coupled to the compression pad 44 for selectively moving the latter relative to the base 20.

For example, the base 20 defines a pair of parallel pad mounting apertures 46 (seen for example in FIG. 8) extending therethrough and an actuator mounting aperture 48 extending parallel to the pad mounting apertures 46. In some embodiments, the pad and actuator mounting apertures 46 and 48 are provided on a line and extend generally perpendicular to the compression surface 16. The actuator mounting aperture 48 is threaded.

Figure 2:
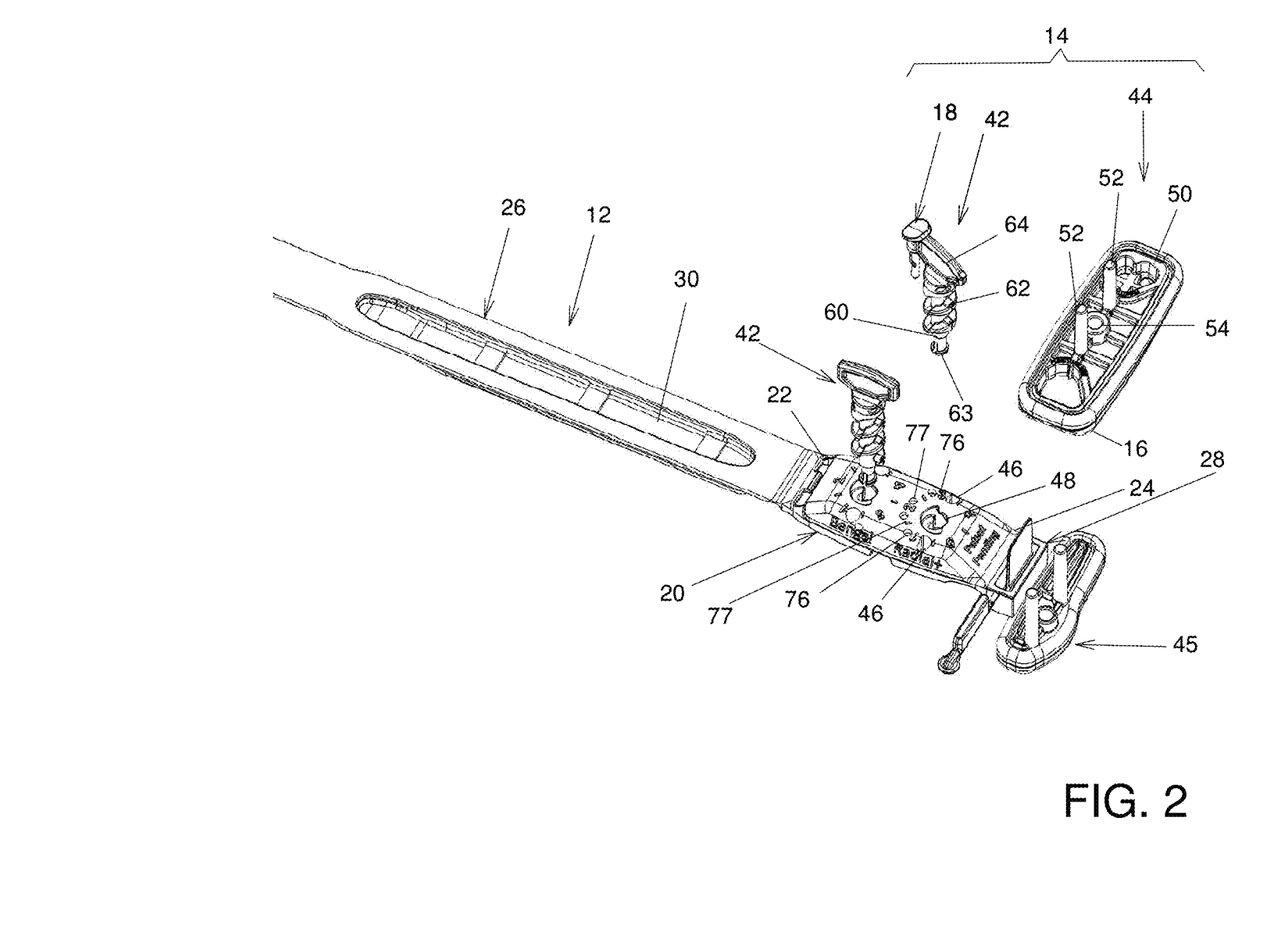
FIG. 2, in a perspective exploded partial view, illustrates the hemostatic device of FIG. 1.

The compression pad 44 includes a pad body 50, defining the compression surface 16, and a pair of pad stems 52 extending therefrom opposed to the compression surface 16. The pad stems 52 are each configured and sized for being substantially snugly received in one of the pad mounting apertures 46 while being longitudinally movable therealong.

The compression surface 16 may have any suitable shape to provide an optimal pressure on the puncture without completely occluding the punctured artery. For example, as better seen for example in FIG. 3, the compression surface 16 is substantially flat and provided with a bump 55 protruding from the remainder thereof.

The pad body 50 defines a generally cylindrical recess 54 generally parallel to the pad stems 52. An opening 56 leads in the recess 54. The opening 56 may be formed by an inward flange 58 so that the opening 56 is smaller in diameter than the remainder of the recess 54.

The actuator 42 includes an actuator stem 60 defining a thread 62 that matches the thread of the actuator mounting aperture 48 so that rotating the actuator stem 60 moves the actuator stem 60 along the actuator mounting aperture 48. The actuator stem 60 is terminated by a head 63 engaging the recess 54 and maintained therein by the flange 58 as the head 62 is larger in diameter near its free end that further away from its free end. The head 62 is rotatable relative to the recess 54 so that the actuator stem 60 may be rotated without rotating the compression pad 44. The actuator stem 60 is also provided with a wing 64 opposed to the head 62 to facilitate rotation of the actuator stem 60 by the fingers of an intended user. However, other structures such as a ribbed button, among others, are usable instead of the wing 64.

Figure 3:
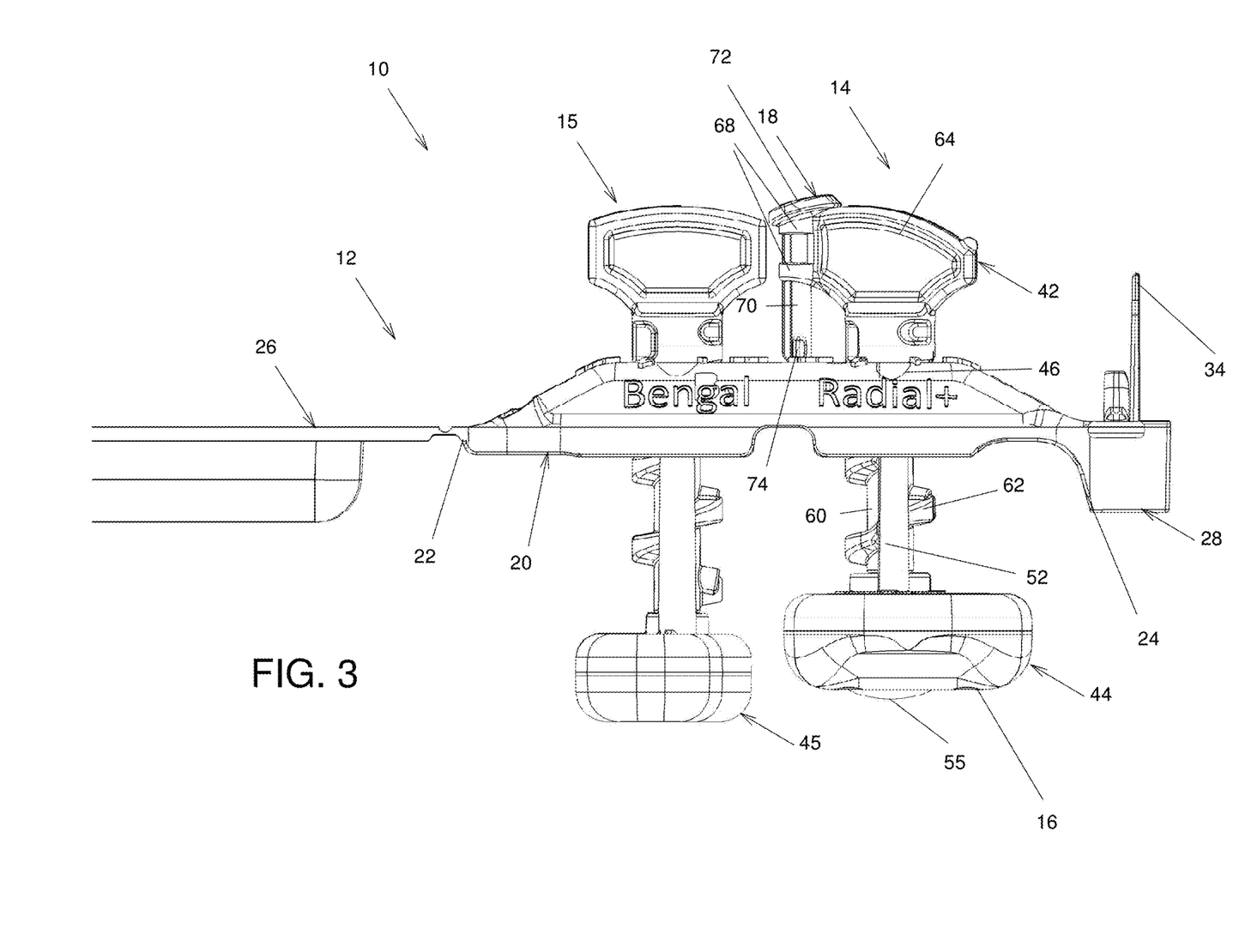
FIG. 3, in a side elevation partial view, illustrates the hemostatic device of FIGS. 1 and 2 with a compression pad thereof in a first position.
Figure 4:
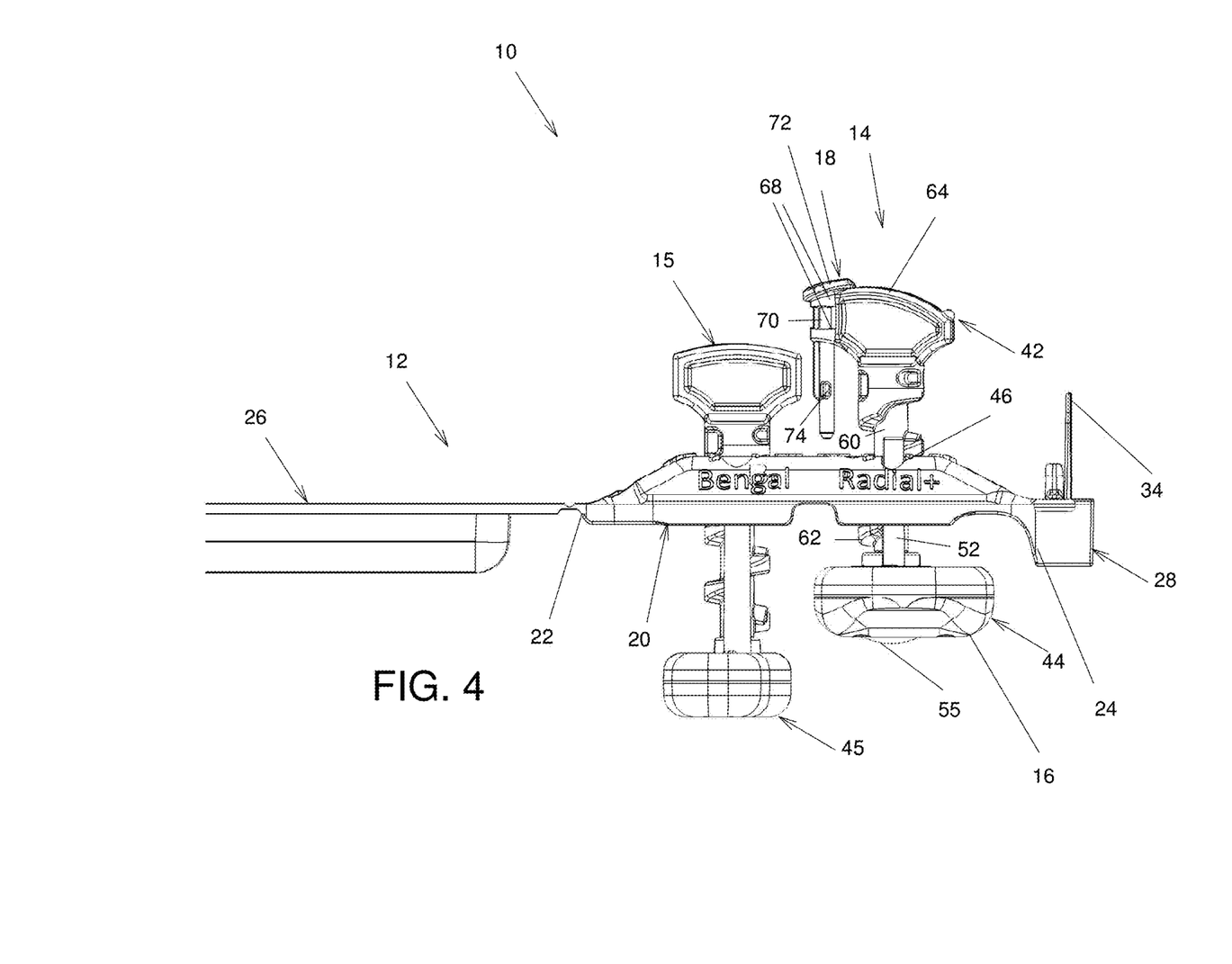
FIG. 4, in a side elevation partial view, illustrates the hemostatic device of FIGS. 1 to 3 with the compression pad thereof in a second position.
Figure 7:
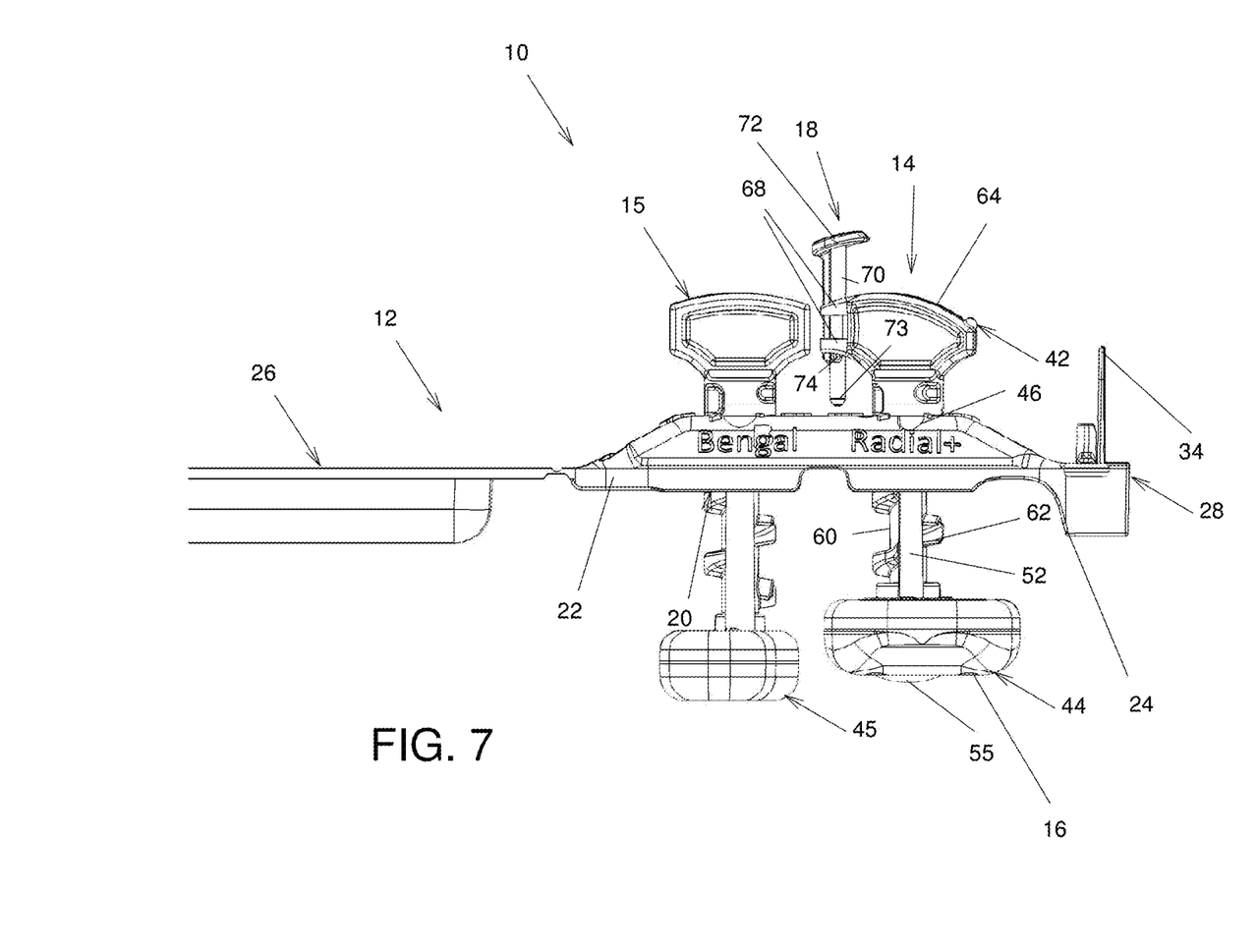
FIG. 7, in a side elevation partial view, illustrates the hemostatic device of FIGS. 1 to 6 with the compression pad thereof in the first position and a lock thereof in an unlocked configuration.
Figure 8:
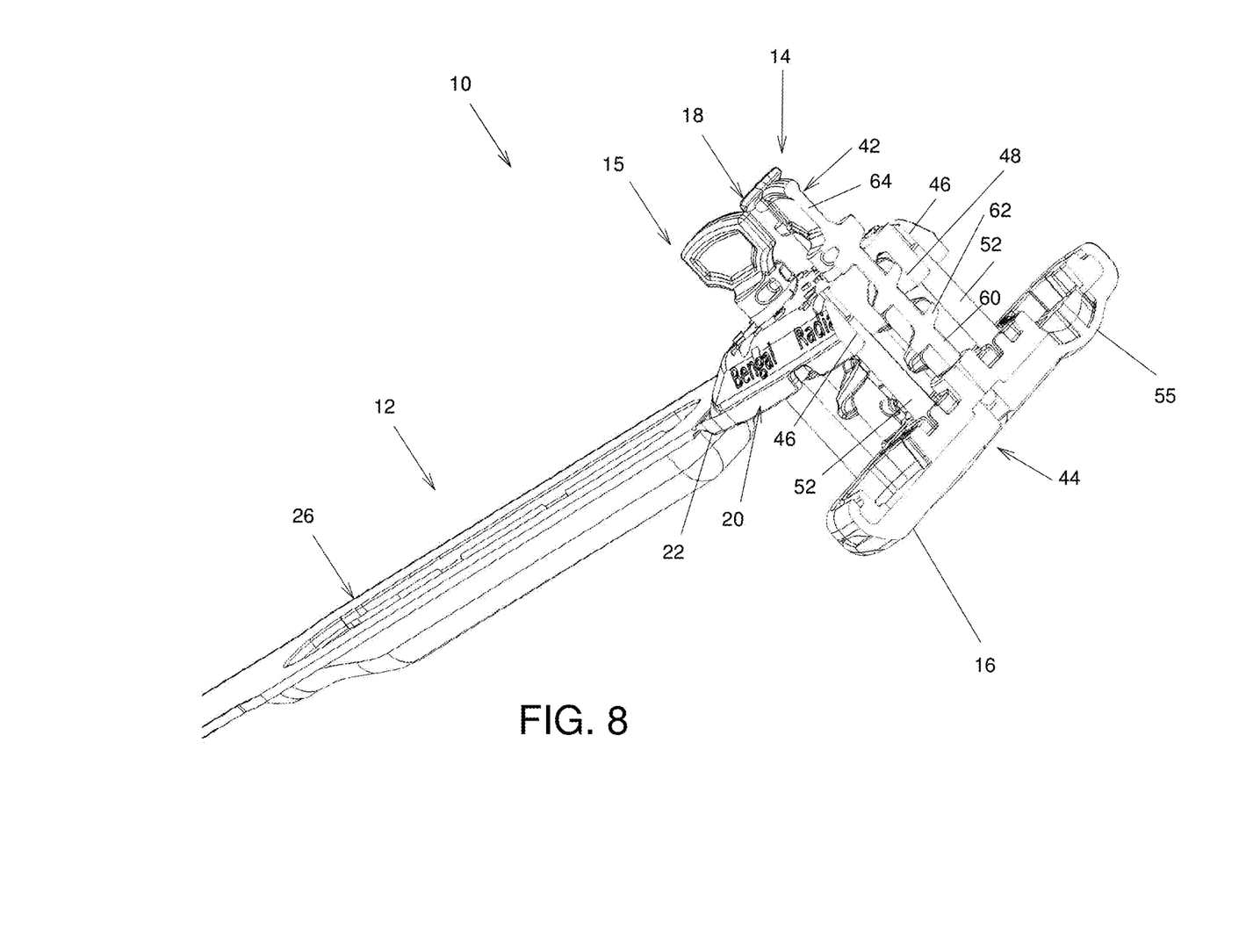

The lock 18 takes the form of an elongated pin 66 mounted to the actuator 42, for example to the wing 64. The pin 66 is movable relative to the wing 64, typically substantially parallel to the actuator stem 60, between a lowered position (as seen in FIGS. 3 and 4) and a raised position (as seen in FIG. 7). The pin 66 is mounted for example in a pair of longitudinally spaced apart pin collars 68 formed in the wing 64 and includes a pin stem 70 provided at one end thereof with a pin head 72 and with a pin tip 73 at the other end thereof. A pin protrusion 74 extends laterally from the pin stem 70 at a location intermediate the pin tip 73 and the pin collar 68 furthest from the pin head 72. The pin head 72 and pin protrusion 74 limit movements of the pin stem 70 in the pin collars 68 between the raised and lowered positions.

Lock apertures 76 are formed in the base 20 facing the pin 66. The lock apertures 76 are provided in a generally circular or arc segment shaped configuration centred on the actuator mounting aperture 48. The lock apertures 76 are each configured and sized to substantially snugly receive the pin 66 at the pin tip 73. By lowering the pin 66 in a lock aperture 76, rotation of the actuator stem 60 is prevented, which achieves a locked configuration. When the pin 66 is raised to disengage the lock aperture 76, an unlocked configuration in which the actuator stem 60 may be rotated relative to the base 20 is achieved. A predetermined number of lock apertures 76 is provided to lock the pin 66 are selected angular positions, corresponding to selected positions of the compression surface 16 relative to the base 20. Indicia 77 may be provided adjacent each lock aperture to identify each lock aperture 76.

In operation, the compression surfaces 16 are moved adjacent a puncture to compress and the strap 26 is closed. Then the actuators 42 can be used to adjust a distance between the compression surfaces 16 and the base 20, which adjusts the pressure exerted on the patient. Once a suitable pressure is exerted, the pin 66 may be lowered in a lock aperture 76 to prevent accidental movements of the compression pad 44 relative to the base 20. Some protocols require that the pressure be gradually released on the puncture. In such cases, once time has come to release the pressure, the pin 66 may be raised, the actuator 42 may be turned to release a bit of pressure, and the pin 66 may be lowered in another lock aperture 76. This process can be repeated until hemostasis has been reached, at which point the bracelet 12 is removed by releasing the strap 26 from the closure 28.

Although the present invention has been described hereinabove by way of preferred embodiments thereof, it can be modified, without departing from the spirit and nature of the subject invention as defined in the appended claims.

What is claimed is:

1. A hemostatic device, the hemostatic device comprising:
a bracelet for enclosing a limb of a patient;
a compression element mounted to the bracelet and defining a compression surface for compressing against the patient, the compression element being movable relative thereto the bracelet so that a distance between the bracelet and the compression surface is varied when the bracelet and compression element are moved relative to each other; and
an actuator for selectively moving the compression element relative to the bracelet between a retracted position and an extended position, wherein the compression surface is closer to the bracelet in the retracted position than in the extended position; and
a lock for selectively locking the compression element and bracelet relative to each other so as to prevent movements between the retracted and extended positions;
wherein the bracelet includes a base defining substantially opposed base first and second ends, the compression element further including a compression pad defining the compression surface, the actuator engaging the base and the compression pad so that the actuator is usable to vary a distance between the compression pad and the base;
wherein the base defines an actuator mounting aperture extending therethrough, the actuator mounting aperture being threaded, the actuator including a threaded stem threadedly engaging the actuator mounting aperture and also engaging the compression pad so that rotating the threaded stem relative to the base changes a distance between the compression pad and the base;
wherein the lock includes a pin mounted to the actuator so as to be movable relative to the threaded stem, the base defining lock apertures formed in the base facing the pin, the lock apertures being provided in one of a generally circular shaped configuration and a generally arc segment shaped configuration centred on the actuator mounting aperture, the lock apertures being configured and sized to receive the pin so that with the pin received in one of the lock apertures, rotation of the threaded stem relative to the base is prevented, and with the pin withdrawn from the lock apertures, the threaded stem is rotatable relative to the base.

2. The hemostatic device as defined in claim 1, wherein the lock is operative for selectively locking the compression element and bracelet relative to each other at discrete positions between the extended and retracted positions.

3. The hemostatic device as defined in claim 1, wherein the compression element is a radial artery compression element configured and sized for compressing a radial artery, the actuator being a radial artery actuator, the hemostatic device further comprising an ulnar artery compression element configured and sized for compressing an ulnar artery and an ulnar artery actuator for selectively moving the compression element relative to the bracelet.

4. The hemostatic device as defined in claim 3, wherein the bracelet includes a base defining a pair of threaded actuator mounting apertures extending therethrough and the radial and ulnar artery compression element each including a respective compression pad, the radial and ulnar actuators each including a respective threaded stem threadedly engaging a respective one of the actuator mounting aperture and also engaging a respective one of the compression pads so that rotating the threaded stems relative to the base changes a distance between the compression pads and the base.

5. The hemostatic device as defined in claim 4, wherein the radial and ulnar artery compression elements are mounted to the base so as to be circumferentially spaced apart from each other when the bracelet is in a closed configuration, facing radially inwardly, towards a centre of a loop formed by the bracelet.

6. The hemostatic device as defined in claim 5, wherein the bracelet further includes a flexible strap extending from the base first end and a closure provided as the base second end, the closure and strap being configured and sized so that the strap is engageable in the closure to close the bracelet to form a loop.

7. The hemostatic device as defined in claim 1, wherein the threaded stem is substantially perpendicular to a circumferential direction extending between the base first and second ends.

8. The hemostatic device as defined in claim 1, wherein the threaded stem is operatively coupled to the compression pad so as to be rotatable relative thereto and axially fixed relative thereto so that the compression pad is movable axially relative to the base as the threaded stem is rotated in the actuator mounting aperture while maintaining a fixed orientation relative to the base.

9. The hemostatic device as defined in claim 8, wherein
the base further defines a pair of pad mounting aperture extending therethrough each extending parallel to the stem mounting aperture; and
the compression pad further includes a pair of pad stems extending opposed to the compression surface, each pad stems being substantially snugly received in one of the pad mounting apertures so as to be longitudinally movable therealong.

10. The hemostatic device as defined in claim 8, wherein the compression pad defines a generally cylindrical recess and an opening leading into the recess, the opening being smaller in diameter than a remainder of the recess, the threaded stem being terminated by a head engaging the recess and maintained therein, the head being rotatable relative to the recess so that the threaded stem may be rotated relative to the base while maintaining fixed a relative orientation between the base and the compression pad.

11. The hemostatic device as defined in claim 1, wherein the threaded stem is provided with a wing opposed to the head compression surface.

12. The hemostatic device as defined in claim 1, wherein indicia are provided adjacent each lock aperture to identify each lock aperture, each indicia being indicative of a relative distance between the base and the compression pad.

13. The hemostatic device as defined in claim 1, wherein the pin is movable relative to actuator substantially parallel to the threaded stem between a lowered position, wherein the pin is engaged in one of the lock apertures, and a raised position, wherein the pin is spaced apart from the base.

14. The hemostatic device as defined in claim 13, wherein the pin is mounted in a pair of spaced apart pin collars formed in the actuator, the pin including a pin stem inserted in the pin collars and terminated by pin head, a pin protrusion extending laterally from the pin stem, the pin head and pin protrusion limiting movements of the pin stem in the pin collars between the raised and lowered positions.

15. The hemostatic device as defined in claim 6, wherein the strap is provided with a deformable portion compressible to provide a cushion when tightened around a wrist of a patient.

\* \* \* \* \*